United States Patent
Kapadia et al.

(10) Patent No.: US 11,857,285 B2
(45) Date of Patent: Jan. 2, 2024

(54) SURGEON INPUT DEVICE FOR MINIMALLY INVASIVE SURGERY

(71) Applicant: Sudhir Prem Srivastava, Frisco, TX (US)

(72) Inventors: Salman Kapadia, Seoni (IN); Venkatachalapathi Rao Salugu, Vijayawada (IN); Sravan Kumar Maddela, Sullurpeta (IN)

(73) Assignee: Sudhir Prem Srivastava

( * ) Notice: Subject to any disclaimer, the term of this patent is extended or adjusted under 35 U.S.C. 154(b) by 399 days.

(21) Appl. No.: 16/906,548

(22) Filed: Jun. 19, 2020

(65) Prior Publication Data

US 2020/0397524 A1 Dec. 24, 2020

(30) Foreign Application Priority Data

Jun. 20, 2019 (IN) .............................. 201911024519

(51) Int. Cl.
*A61B 34/00* (2016.01)
*A61B 34/37* (2016.01)
(Continued)

(52) U.S. Cl.
CPC .............. *A61B 34/74* (2016.02); *A61B 34/37* (2016.02); *A61B 2017/0042* (2013.01);
(Continued)

(58) Field of Classification Search
CPC ... A61B 34/74; A61B 34/37; A61B 2034/301; A61B 2034/302; A61B 2034/741; A61B 2034/742; A61B 2090/064; A61B 2017/0042; A61B 2562/0219; A61B 2562/0223
(Continued)

(56) References Cited

U.S. PATENT DOCUMENTS 5,844,415 A * 12/1998 Gershenfeld ..... B60R 21/01532
340/870.37
2017/0095236 A1* 4/2017 Sharma .................. A61B 17/00
(Continued)

FOREIGN PATENT DOCUMENTS

CN 108472083 A * 8/2018 ....... A61B 17/00234

*Primary Examiner* — Carl H Layno
*Assistant Examiner* — Michael J Lau
(74) *Attorney, Agent, or Firm* — Jose Cherson Weissbrot

(57) ABSTRACT

A surgeon input device for controlling a robotic surgical system is disclosed herein. The surgeon input device comprising a housing and at least one sensor disposed within the housing. The at least one sensor, in operative communication with an electromagnetic signal transmitter, configured to detect at least one of a position and orientation of a surgeon's hand within a predefined electromagnetic field generated by the electromagnetic signal transmitter. The surgeon input device further comprising at least one button protruding out of the housing, where the at least one button configured to open and close an end-effector of a surgical instrument and at least one sensor disposed within the housing, where the at least one sensor configured to detect a compression and decompression of the at least one button and send a signal via a sensor wire to a control system to regulate opening and closing of the end effector of the surgical instrument.

9 Claims, 8 Drawing Sheets

(51) Int. Cl.
  *A61B 34/30*      (2016.01)
  *A61B 90/00*      (2016.01)
  *A61B 17/00*      (2006.01)

(52) U.S. Cl.
  CPC ... *A61B 2034/301* (2016.02); *A61B 2034/302* (2016.02); *A61B 2034/741* (2016.02); *A61B 2034/742* (2016.02); *A61B 2090/064* (2016.02); *A61B 2562/0219* (2013.01); *A61B 2562/0223* (2013.01)

(58) Field of Classification Search
  USPC .......................................................... 606/167
  See application file for complete search history.

(56) References Cited

U.S. PATENT DOCUMENTS

2019/0308097 A1* 10/2019 Yamano .................... G06F 3/02
2020/0015917 A1*  1/2020 Cavalier ................ B25J 9/1689

* cited by examiner

SURGEON INPUT DEVICE FOR MINIMALLY INVASIVE SURGERY

CROSS-REFERENCE TO RELATED APPLICATION

This application claims priority to Indian Patent Application No. 201911024519, filed on Jun. 20, 2019, the contents of which are incorporated into the present application by reference.

TECHNICAL FIELD

The present disclosure generally relates to a robotic assisted surgical system for minimally invasive surgery. More particularly, the disclosure relates to a surgeon input device for directing movement of the robotic assisted surgical system during the robotic assisted surgical procedures.

BACKGROUND

This section is intended to introduce the reader to various aspects of art that may be related to various aspects of the present disclosure, which are described below. This disclosure is believed to be helpful in providing the reader with background information to facilitate a better understanding of the various aspects of the present disclosure. Accordingly, it should be understood that these statements are to be read in this light, and not just as admissions of prior art.

Robotically assisted surgical systems have been adopted worldwide to replace conventional surgical procedures to reduce amount of extraneous tissues that may be damaged during surgical or diagnostic procedures, thereby reducing patient recovery time, patient discomfort, prolonged hospital tenure, and particularly deleterious side effects. In robotic assisted surgeries, the surgeon typically operates a hand controller/a master controller/a surgeon input device at a surgeon console to seamlessly capture and transfer complex actions performed by the surgeon giving the perception that the surgeon is directly articulating surgical tools/surgical instruments to perform the surgery. The surgeon operating on the surgeon console may be located at a distance from a surgical site or may be located within an operating theatre where the patient is being operated.

The robotically assisted surgeries have revolutionized the medical field and one of the fastest growing sectors in medical device industry. However, the major challenge in robotically assisted surgeries is to ensure the safety and precision during the surgery. One of the key areas of robotically assisted surgeries is the development of surgical robots for minimally invasive surgery. Over the last couple of decades, surgical robots have evolved exponentially and has been a major area of innovation in the medical device industry.

The robotically assisted surgical systems may comprise of multiple robotic arms aiding in conducting robotic assisted surgeries. The surgeon controls the robotic arm and the instruments mounted on it by using the surgeon console. The surgeon console comprises of visualization system to allow the surgeon to perform the surgery. Further, the hand controllers/the master controllers/the surgeon input devices are integrated with the surgeon console which the surgeon maneuvers to perform the surgery.

Performing surgery at the surgeon console creates new challenges. One challenge is the ergonomics of the console to allow the surgeon to perform the surgery for long duration without any fatigue. During surgery, the surgeon often requires to be seated into an exhaustive posture for many hours due to the hardware structure of such surgeon consoles.

In the light of aforementioned challenges, there is a need for a robotic surgical system with improved surgeon input device, such as sensor based surgeon input device to overcome the disadvantages of mechanical hands manipulators and thus allows the surgeon to change/adjust their sitting posture based on the surgeon's comfort.

SUMMARY OF THE DISCLOSURE

The present disclosure seeks to provide a surgeon input device for controlling a robotic surgical system.

A surgeon input device for controlling a robotic surgical system is disclosed herein. The surgeon input device comprising a housing and at least one sensor disposed within the housing. The at least one sensor, in operative communication with an electromagnetic signal transmitter, configured to detect at least one of a position and orientation of a surgeon's hand within a predefined electromagnetic field generated by the electromagnetic signal transmitter. The surgeon input device further comprising at least one button protruding out of the housing, where the at least one button configured to open and close an end-effector of a surgical instrument and at least one sensor disposed within the housing, where the at least one sensor configured to detect a compression and decompression of the at least one button and send a signal via a sensor wire to a control system to regulate opening and closing of the end effector of the surgical instrument.

Optionally, the housing comprising a capacitive sensor to detect presence of the surgeon's hand.

Optionally, the at least one sensor is an electromagnetic sensor or an Inertial Measurement Unit (IMU) sensor.

Optionally, the surgeon input device in operative communication with the control system via a wireless means such as Bluetooth.

Optionally, the surgeon input device further comprising a support structure positioned within the housing and a lever with a spring affixed in a hollow recess of the support structure by means of a shaft. The at least one button having an extruding portion configured to push the lever, wherein the at least one sensor detects the lever being pushed to send a signal to the control system to regulate the opening and closing of the jaws of the end effector of the surgical instrument.

Optionally, the at least one sensor is an optical sensor.

Optionally, the at least one sensor is a force sensor.

Optionally, the surgeon input device configured to provide an input to the control system to transform motion of the surgeon's hand into motion of the end-effector of the surgical instrument.

Optionally, the surgeon input device is made of polycarbonate plastic.

Optionally, the housing comprising an outer surface configured to be gripped by the surgeon's hand and to facilitate translation and rotation of the housing by the surgeon's hand.

Additional aspects, advantages, features, and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

To further clarify advantages and features of the present disclosure, a more particular description of the disclosure will be rendered by reference to specific embodiments thereof, which is illustrated in the appended drawings. It is appreciated that these drawings depict only typical embodiments of the disclosure and are therefore not to be considered limiting of its scope. The disclosure will be described and explained with additional specificity and detail with the accompanying drawings in which.

DETAILED DESCRIPTION

Figure 1A:
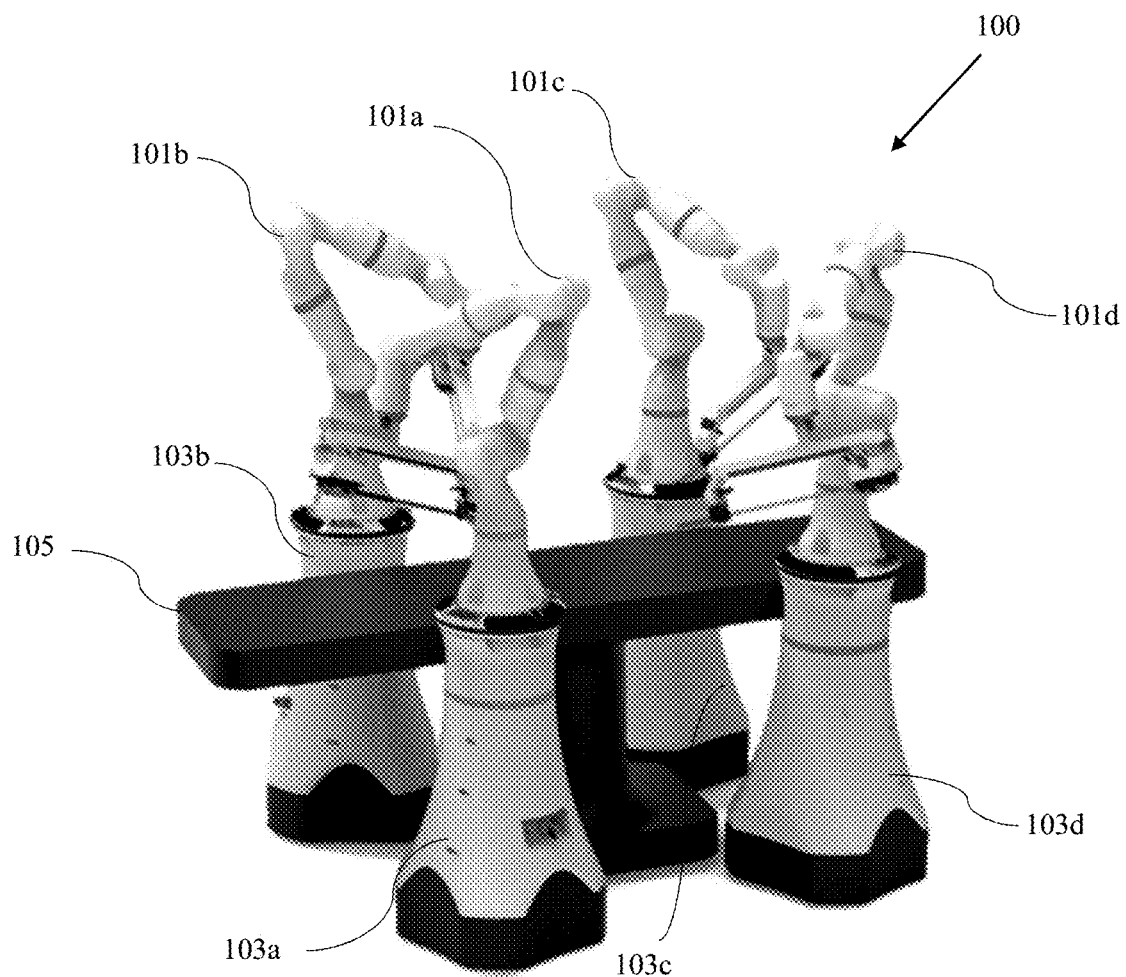
FIG. 1(a) illustrates a schematic diagram of multiple robotic arms of a robotic surgical system in accordance with an embodiment of the disclosure.

For the purpose of promoting an understanding of the principles of the disclosure, reference will now be made to the embodiment illustrated in the drawings and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof. Throughout the patent specification, a convention employed is that in the appended drawings, like numerals denote like components.

Reference throughout this specification to "an embodiment", "another embodiment", "an implementation", "another implementation" or similar language means that a particular feature, structure, or characteristic described in connection with the embodiment is included in at least one embodiment of the present disclosure. Thus, appearances of the phrase "in an embodiment", "in another embodiment", "in one implementation", "in another implementation", and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this disclosure belongs. The apparatus, system, and examples provided herein are illustrative only and not intended to be limiting.

The terms "a" and "an" herein do not denote a limitation of quantity, but rather denote the presence of at least one of the referenced items. Further, the term sterile barrier and sterile adapter denotes the same meaning and may be used interchangeably throughout the description.

Embodiments of the disclosure will be described below in detail with reference to the accompanying drawings.

The disclosure relates to a robotic surgical system for minimally invasive surgery. The robotic surgical system will generally involve the use of multiple robotic arms. One or more of the robotic arms will often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). One or more of the robotic arms will often be used to support one or more surgical image capture devices such as an endoscope (which may be any of the variety of structures such as a laparoscope, an arthroscope, a hysteroscope, or the like), or optionally, some other imaging modality (such as ultrasound, fluoroscopy, magnetic resonance imaging, or the like).

FIG. 1(a) illustrates a schematic diagram of multiple robotic arms of a robotic surgical system in accordance with an embodiment of the disclosure. Specifically, FIG. 1 illustrates the robotic surgical system (100) having four robotic arms (101a), (101b), (101c), (101d) mounted on four robotic arm carts (103a), (103b), (103c), (103d) around an operating table (105). The four-robotic arms (101a), (101b), (101c), (101d) as depicted in FIG. 1(a) is for illustration purpose and the number of robotic arms may vary depending upon the type of surgery or the robotic surgical system. The four robotic arms (101a), (101b), (101c), (101d) are arranged along the operating table (105) and may be arranged in different manner but not limited to the robotic arms (101a), (101b), (101c), (101d) arranged along the operating table (101) or the robotic arms (101a), (101b), (101c), (101d) separately mounted on the four robotic arm carts (103a), (103b), (103c), (103d) or the robotic arms (101a), (101b), (101c), (101d) mechanically and/or operationally connected with each other or the robotic arms (101a), (101b), (101c), (101d) connected to a central body (now shown) such that the robotic arms (101a), (101b), (101c), (101d) branch out of the central body (now shown).

Figure 1B:
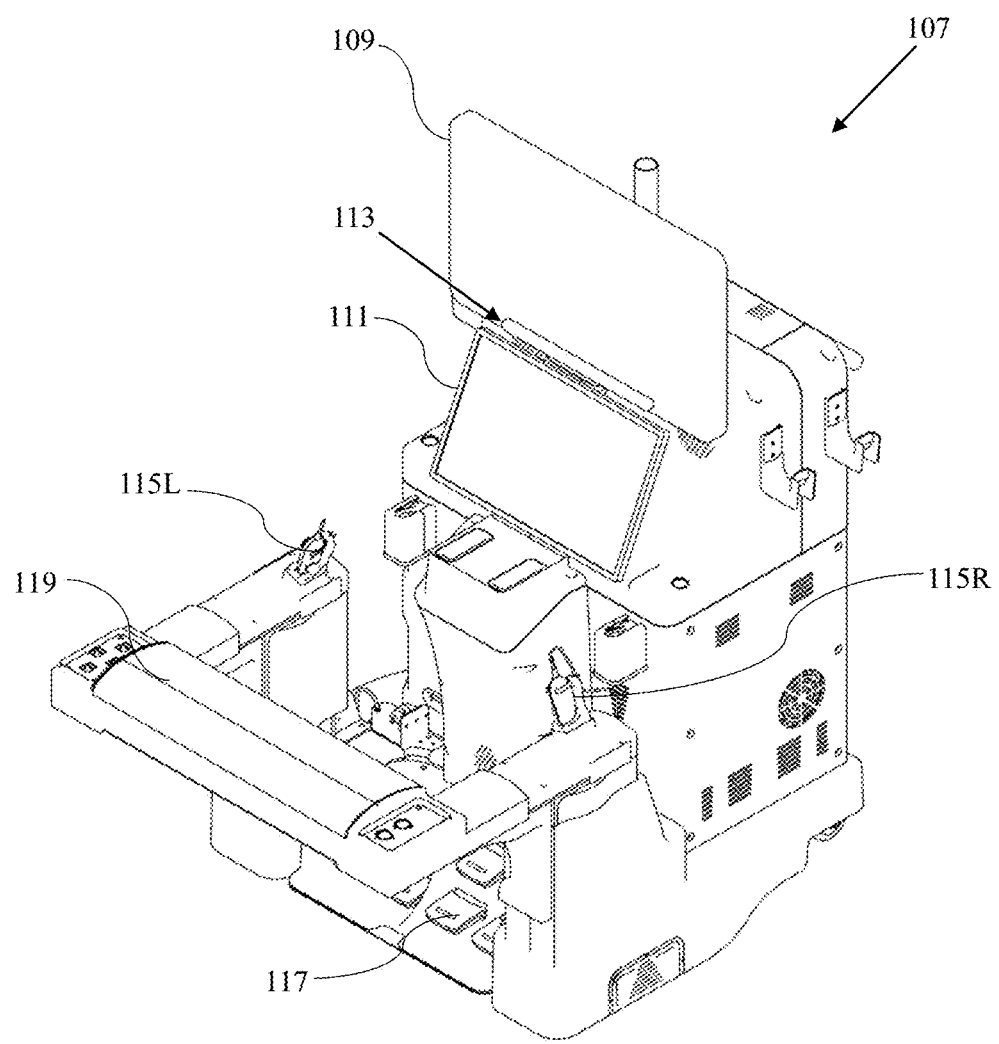
FIG. 1(b) illustrates a schematic diagram of a surgeon console of the robotic surgical system in accordance with an embodiment of the disclosure.
Figure 2:
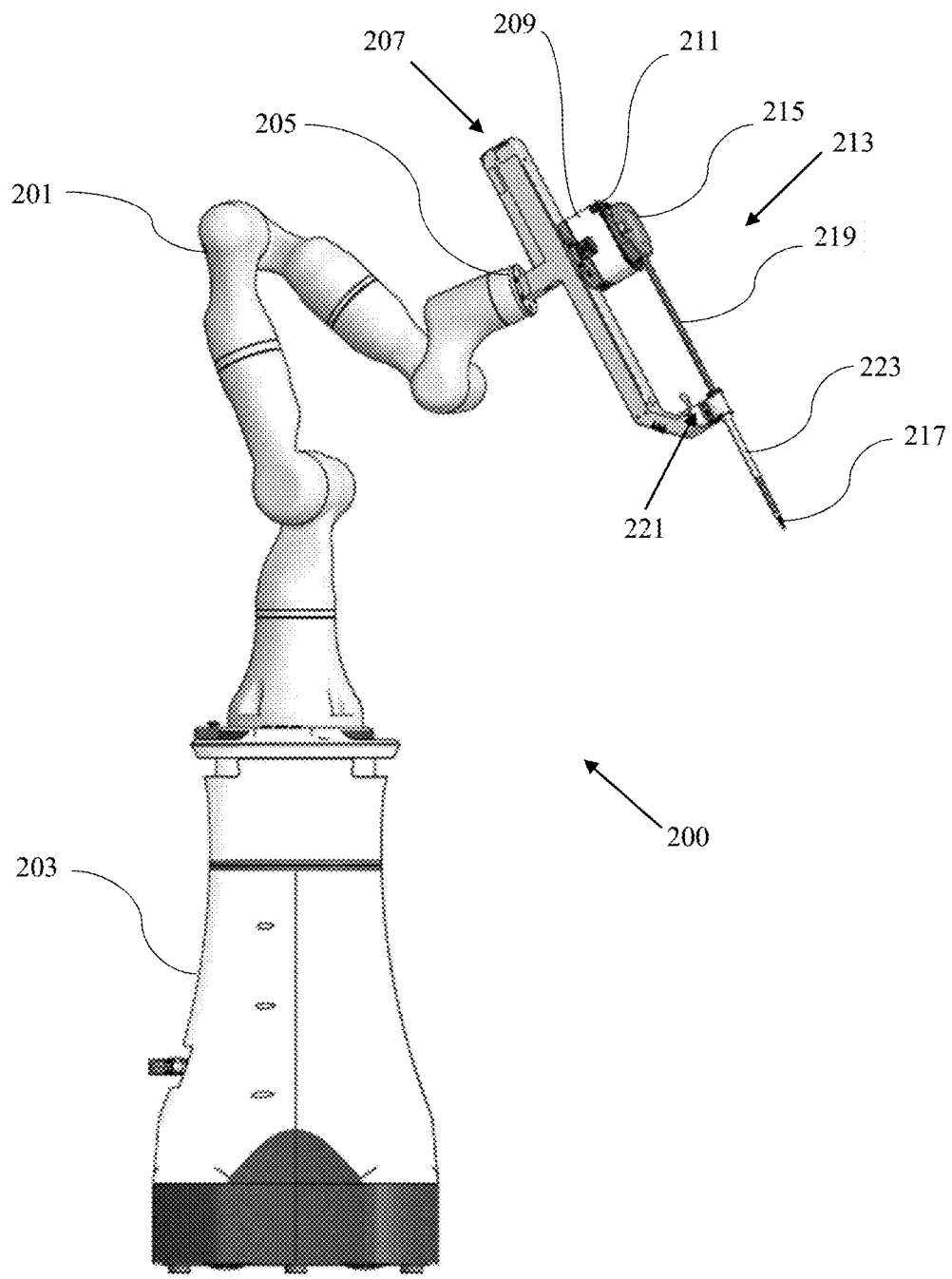
FIG. 2 illustrates a perspective view of a tool interface assembly mounted on a robotic arm in accordance with an embodiment of the disclosure.

FIG. 1(b) illustrates a schematic diagram of a surgeon console of the robotic surgical system in accordance with an embodiment of the disclosure. The surgeon console (107) aids the surgeon to remotely operate the patient lying on the operating table (105) by controlling various surgical instruments and endoscope mounted on the robotic arms (101a), (101b), (101c), (101d). The surgeon console (107) may be configured to control the movement of surgical instruments (as shown in FIG. 2) while the instruments are inside the patient body. The surgeon console (107) may comprise of at least an adjustable viewing means (109) and (111) but not limited to 2D/3D monitors, wearable viewing means (not shown) and in combination thereof. The surgeon console (107) may be equipped with multiple displays which would not only show 3D high definition (HD) endoscopic view of a surgical site at the operating table (105) but may also shows additional information from various medical equipment's which surgeon may need during the robotic surgery. Further, the viewing means (109) and (111) may provide various modes of the robotic surgical system (100) but not limited to identification of number of robotic arms attached, current surgical instruments type attached, current instruments end effector tip position, collision information along with medical data like ECG, ultrasound display, fluoroscopic images, CT, MRI information and the like.

The surgeon console (107) may further comprise of an eye tracking camera system (113) for detecting the direction of the surgeon's eye gaze and accordingly activates/deactivates the surgical instruments control. Furthermore, the surgeon console (107) may comprise of mechanism for controlling the robotics arms but not limited to one or more surgeon input devices (115L) and (115R), one or more foot pedal controllers (117), a clutch mechanism (not shown), and in combination thereof. The surgeon input devices (115L) and (115R) at the surgeon console (107) are required to seamlessly capture and transfer complex actions performed by surgeon giving the perception that the surgeon is directly articulating the surgical instruments. The different controllers may require for different purpose during the surgery. In some embodiments, the surgeon input devices (115L) and (115R) may be one or more manually-operated input devices, such as a joystick, exoskeletal glove, a powered and gravity-compensated manipulator, or the like. The surgeon may sit on a resting apparatus such as a chair (not shown) in proximity to the surgeon console (107) such that the surgeon's arms may rest on an arm rest (119), while controlling the surgeon console (107). The chair may be adjustable with means in height, elbow rest and the like according to the ease of the surgeon and also various control means may be provided on the chair and the arm rest (119). Further, the surgeon console (107) may be at a one location inside an operation theatre or may be placed at any other location in the hospital provided connectivity to the robotics arms (101a, 101b, 101c, 101d) via wired or wireless means is maintained.

Figure 1C:
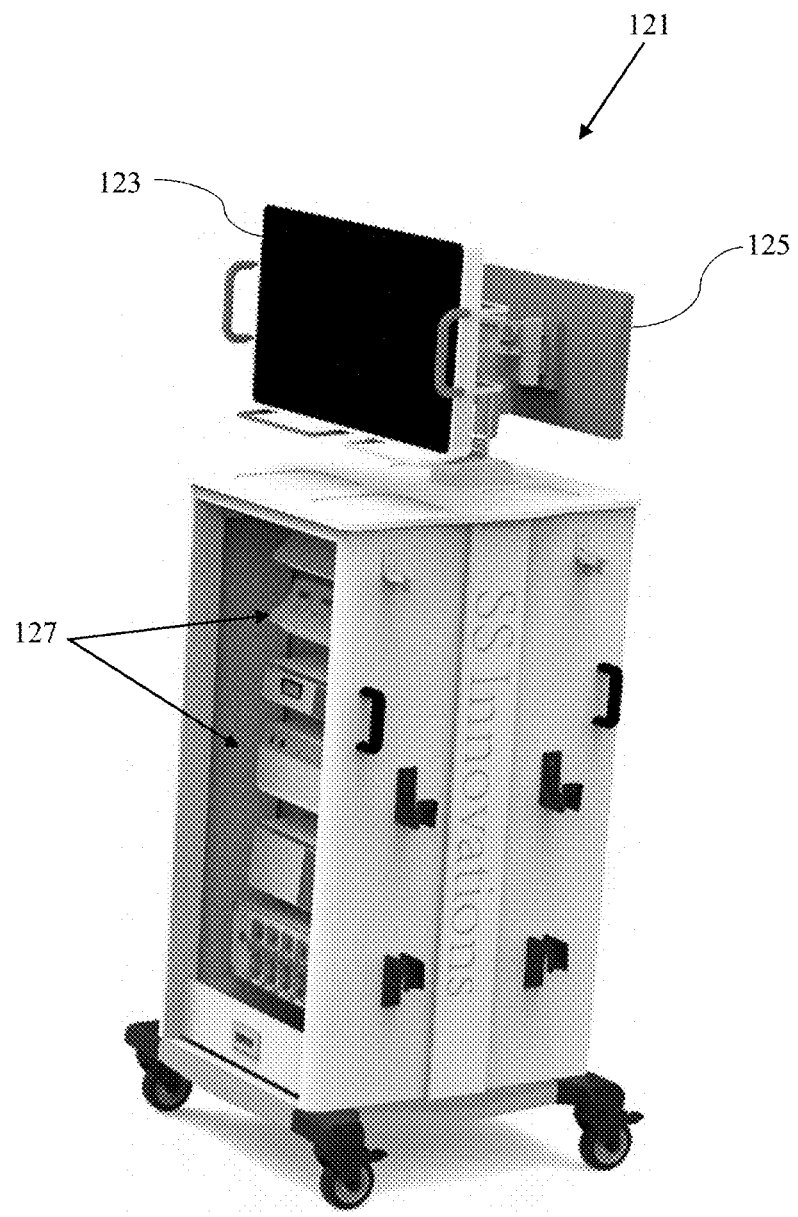
FIG. 1(c) illustrates a schematic diagram of a vision cart of the robotic surgical system in accordance with an embodiment of the disclosure.

FIG. 1(c) illustrates a schematic diagram of a vision cart of the robotic surgical system in accordance with an embodiment of the disclosure. The vision cart (121) is configured to display the 2D and/or 3D view of the surgery captured by an endoscope mounted on any of the robotic arm. The vision cart (121) may be adjusted at various angles and heights depending upon the ease of view. The vison cart (121) may have various functionality but not limited to providing touch screen display, preview/recording/playback provisions, various inputs/outputs means, 2D to 3D converters and the like. The vision cart (121) may include a 3D monitor (123) to view a surgical site from outside the patient's body. One of the robotics arms typically engage a surgical instrument that has a video-image-capture function (i.e., a camera instrument) for displaying the captured images on the vision cart (121). In some robotic surgical system configurations, the camera instrument includes an optics that transfer the images from the distal end of the camera instrument to one or more imaging sensors (e.g., CCD or CMOS sensors) outside of the patient's body. Alternatively, the imaging sensor(s) may be positioned at the distal end of the camera instrument, and the signals produced by the sensor(s) may be transmitted along a wire or wirelessly for processing and display on the vision cart (121). A 2D monitor (125) may be placed at the rear side of the vision cart (121) that enables a spectator or other non-operating surgeons to view a surgical site from outside the patient's body. The vision cart (121) may comprise of various shelfs (127) which may be provided to keep a camera processing unit, a robotic arms control box, a robotic system processing unit, power back-up units and the like.

FIG. 2 illustrates a perspective view of a tool interface assembly mounted on a robotic arm in accordance with an embodiment of the disclosure. The tool interface assembly (200) is mounted on the robotic arm (201) of the robotic surgical system (100). The tool interface assembly (200) is one of the main components for performing the robotic surgery on a patient. The robotic arm (201) as shown in FIG. 2 is shown for the illustration purpose only and other robotic arms with different configurations, degree of freedom (DOF) and shapes may be used. The robotic arm (201) is mounted on a robotic arm cart (203), on the opposite end of tool interface assembly (200), such that the robotic arm (201) may be shifted freely within an operating theater.

The tool interface assembly (200), as depicted by FIG. 2, comprises of an ATI (Arm Tool Interface) connector (205) which facilitates a tool interface (207) to operationally connect with the robotic arm (201). The tool interface assembly (200) further comprises of an actuator (209) mounted on a guiding mechanism (not shown) provided on the tool interface (207) and capable of linearly moving along the guiding mechanism such as a guide rail. The movement of the actuator (209) along the guiding mechanism of the tool interface (207) is controlled by the surgeon with help of surgeon input device (115L, 115R) on the surgeon console (107) as shown in FIG. 1(b). A sterile adapter (211) is releasably mounted on the actuator (209) to separate a non-sterile part of the robotic arm (201) from a sterile surgical instrument (213). A locking mechanism (not shown) is provided to releasably lock and unlock the sterile adapter (211) with the actuator (209). The sterile adapter (211) detachably engages with the actuator (209) which drives and controls of the surgical instrument (213) in a sterile field. The surgical instrument (213) may also be capable to be releasably lock/unlock or engages/disengages with the sterile adapter (211) by means of a push button (not shown) provided on the surgical instrument (213).

The surgical instrument (213) includes a housing (215), an end effector (217) and an elongated shaft (219) connecting the housing (215) to the end effector (217). The surgical instrument (213) may also contain a stored (e.g., on a semiconductor memory inside the instrument) information that may be permanent or may be updatable by a processor of a robotic surgical system (100). The end effector (217) may be an instrument associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments further provide an articulated support for the surgical instrument (213) such that the position and orientation of the surgical instrument (213) may be manipulated with one or more mechanical degrees of freedom in relation to the elongated shaft (219).

A cannula locking assembly (221) is provided on the tool interface (207) and is configured to lock and unlock a cannula (223) having a hollow body. During a surgery, the surgical instrument (213) is mounted on the sterile adapter (211) and the elongated shaft (219) of the surgical instrument (213) is inserted through the hollow body of the cannula (223). For example, the cannula locking assembly (221) comprises of flap like body which receives the cannula (223) and secures the cannula (223) thereon. Alternatively, the cannula locking assembly (221) may have a circular body for receiving the cannula (223) and comprises of grooves to grip the cannula (223) at a stationary position.

Figure 3:
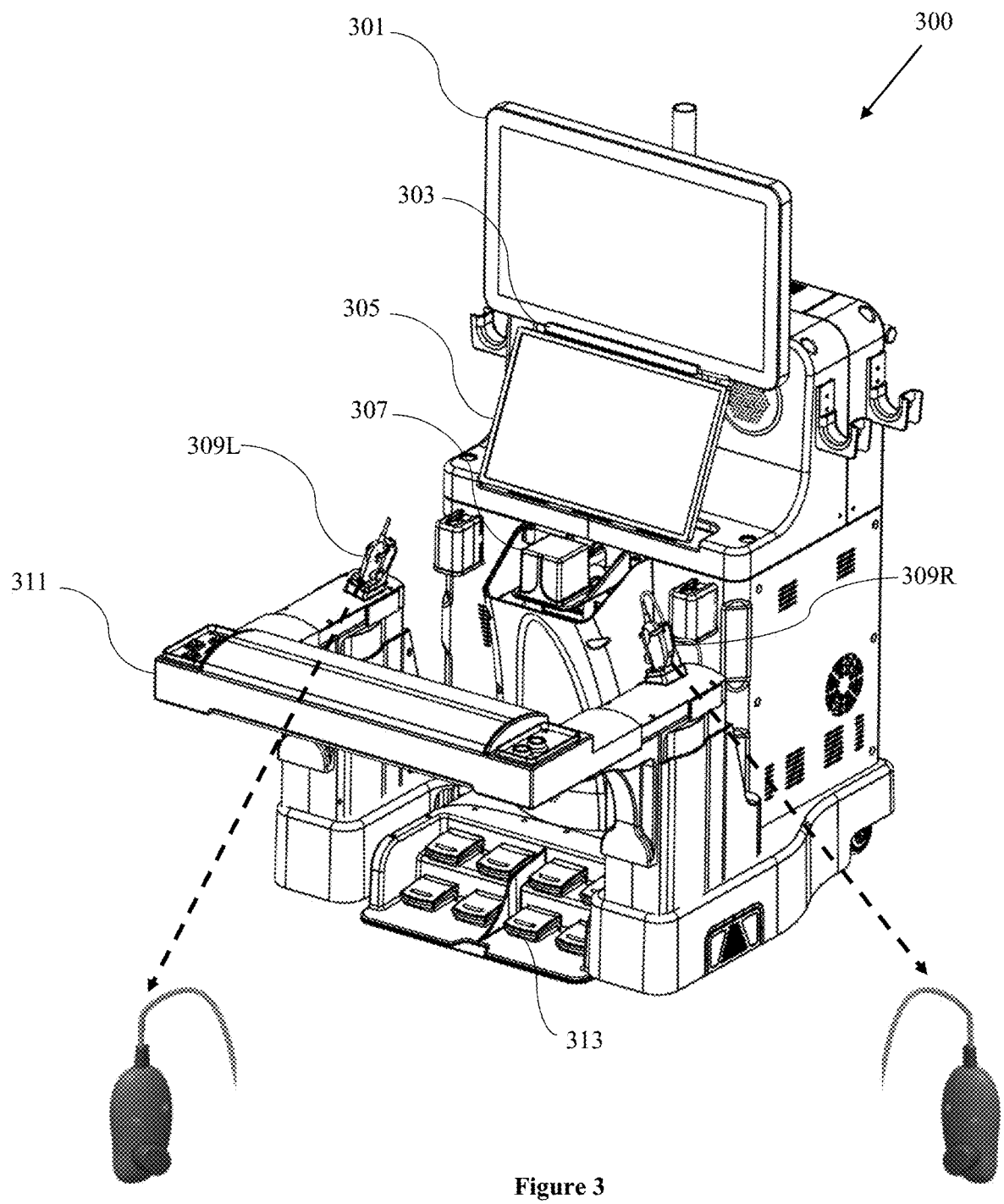
FIG. 3 illustrates a perspective view of a surgeon console with left and right surgeon input device in accordance with an embodiment of the disclosure.

FIG. 3 illustrates a perspective view of a surgeon console with surgeon input device in accordance with an embodiment of the disclosure. The surgeon console (300) may include a 3D monitor (301), an eye tracking camera system (303), a 2D monitor (305), at least one electromagnetic signal transmitter (307), a left hand surgeon input device (309L), a right hand surgeon input device (309R), a surgeon's hand rest (311), and a foot pedal switch assembly (313).

The 3D monitor (301) may be equipped to not only show 3D high definition (HD) endoscopic view of a surgical site at an operating table but may also shows additional information from various medical equipment's which surgeon may need during the robotic surgery. Similarly, the 2D monitor (305) may be placed at the below the 3D monitor (301) that enables the surgeon to view additional details regarding the robotic surgery. The eye tracking camera system (303) may be configured to detect the direction of the surgeon's eye gaze and accordingly activates/deactivates the surgical instruments control.

The electromagnetic signal transmitter (307) may be capable of transmitting an electromagnetic signal at a predefined boundary around the surgeon console (300). The predefined boundary of the electromagnetic signal may be varied around the surgeon console by a user/surgeon. Also, the predefined boundary of the electromagnetic signal may be varied dynamically around the surgeon console by a user/surgeon during the surgery. Further, the variation of the predefined boundary of the electromagnetic signal is facilitated by a processor/a control system configured in the surgeon console (300). According to an embodiment, the electromagnetic signal transmitter (307) may be capable of moving in x, y, and z directions. The electromagnetic signal transmitter (307) movement in x, y, and z directions may be facilitated by plurality of actuators such as linear actuator, telescopic actuator, and the like. The electromagnetic signal transmitter (307) position may be adjusted in x, y, and z direction before the surgery based on the surgeon body habitus, ease, and the like. According to a specific embodiment, the electromagnetic signal transmitter (307) position in x, y, and z directions may be adjusted dynamically during the surgery when the surgeon hand holding the left and right surgeon input device (309L, 309R) may tend to move beyond the predefined boundary of the electromagnetic signal.

The foot pedal switch assembly (313) includes several pedals which may be used for various purposes during surgery such as for clutching, toggling, cautery control, endoscope zoom in & out and the like. The left hand surgeon input device (309L) and the right hand surgeon input device (309R) may collectively referred as a surgeon input device (400) throughout the disclosure, including claims and will be discussed later in more detail.

A surgeon may sit on a chair (not shown) to manipulates the surgical instruments/tools (not shown) via the hand surgeon input devices (309L & 309R). The surgeon may sit on the chair (not shown) in proximity to the surgeon console (107) such that the surgeon's arms may rest on an arm rest (311), while controlling the surgeon console (300).

Figure 4A:
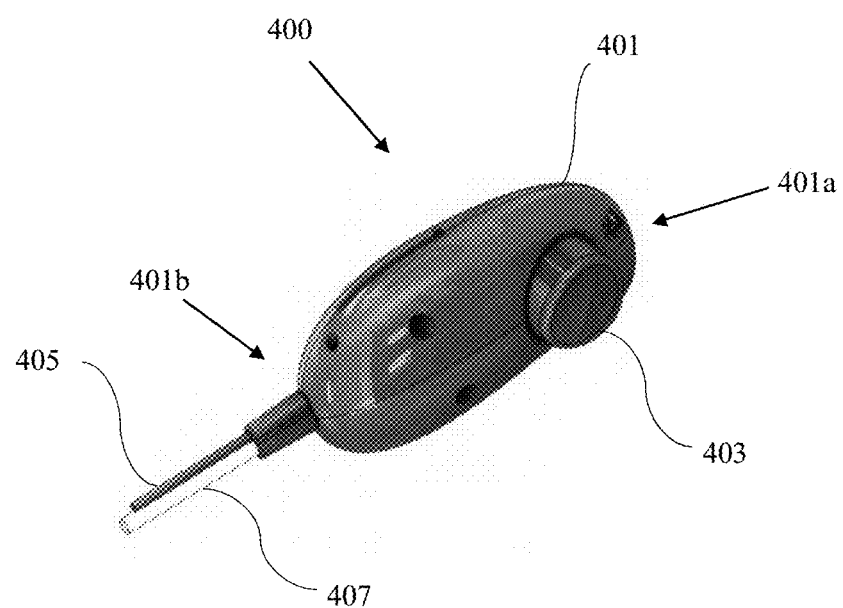
FIG. 4(a) illustrates a surgeon input device in accordance with an embodiment of the disclosure.

FIG. 4(a) illustrates a surgeon input device in accordance with an embodiment of the disclosure. The surgeon input device (400) may include a left hand surgeon input device (309L) and a right hand surgeon input device (309R) illustrated in FIG. 3. Both the surgeon input device (309L), (309R) are identical in nature and comprises of same assembly and functionality, which is explained below. The surgeon input device (400) may comprise of a housing (401), a button (403), a sensor wire (405), and a sensor (407). The surgeon input device (400) may be considered as a hand held device connected to the surgeon console (300) by a wire.

The housing (401) is an outer body to envelope all the aforesaid components of the surgeon input device (400). The housing (401) comprises of a first end (401a) and a second end (401b) and extending along a length defined by a longitudinal axis between the first end (401a) and the second end (401b). Also, the housing (401) extending along a width defined along a transverse axis that extends transverse to the longitudinal axis, where the length being greater than the width of the housing (401).

The housing (401) may be made of any suitable resilient material such as a thermoplastic. In accordance to a specific embodiment of the disclosure, the housing (401) is made of polycarbonate plastic. The housing (401) may be painted or may have a protective coating such as a plastic spray paint. In accordance with an embodiment, the process of coating may be used to coat the housing (401) such as to form a protective coating of plastic paint on the surface of the housing (401). The housing (401) may be of any suitable size such that the surgeon input device (400) fits the hand of the surgeon. The housing (401) may be of a suitable thickness providing sufficient strength. The housing (401) may be of any shape to fit the hands of the surgeon. In accordance to a specific embodiment of the disclosure, the housing (401) is oval shaped.

According to an embodiment, the housing (401) comprising an outer surface configured to be gripped by the surgeon's hand and to facilitate translation and rotation of the housing (401) by the surgeon's hand. The outer surface of the housing (401) may comprise of contours or grooves for the surgeon's hand which may assist the surgeon to grip the surgeon input device (400).

The button (403) is positioned on one of the surfaces of the housing (401) and may protrude outwards from the housing (401). The button (403) is configured to be pressed by the surgeon to close a jaw of an end-effector (shown in FIG. 2) of any surgical instruments. The jaws may open when the surgeon releases the bottom (403). The button (403) may also referred to as a pinch button for opening and closing function of a jaw of the end effector. In accordance to a specific embodiment of the disclosure, the button (403) is circular shaped and made of polycarbonate plastic.

The sensor (407) may be an electromagnetic sensor probe capable of detecting the electromagnetic signal from the electromagnetic signal transmitter (307) located at the surgeon console (300). According to an embodiment, the sensor (407) is a tracking sensor.

The sensor wire (405) may be composed of one or more wires (not shown). The sensor wire (405) may be used for carrying power to the surgeon input device (400). The sensor wire (405) may be used to transport signals or information between the control system and the electronics or sensors within the surgeon input device (400).

Figure 4B:
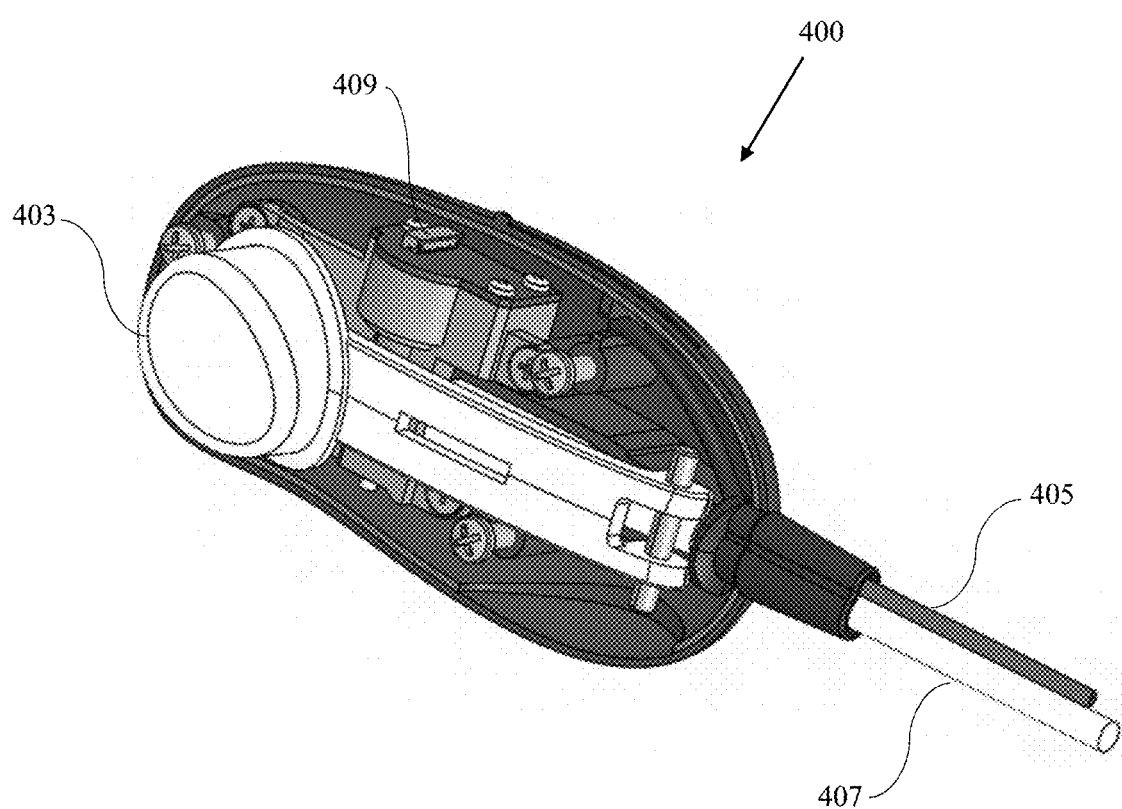
FIG. 4(b) illustrates an internal view of the surgeon input device in accordance with an embodiment of the disclosure.

FIG. 4(b) illustrates an internal view of the surgeon input device in accordance with an embodiment of the disclosure.

The housing (401) as shown in FIG. 4(a) is removed so that internal components of the surgeon input device (400) can be seen.

The surgeon input device (400) further comprises of at least one sensor (409) disposed within the housing (401) to sense the compression and decompression of the pinch button (403) by the surgeon. The at least one sensor (409) may be an optical sensor which senses the compression and decompression of the pinch button (403) and may sends a signal via sensor wire (405) to a control system to control opening and closing of the jaws of the end effectors of the surgical instruments. Further, the at least one sensor (409) may be a force sensor, encoder, and the like. Also, the power source such as a battery may be embedded inside the surgeon input device (400). Alternatively, the surgeon input device (400) may be wireless connected with the control system by means of Bluetooth, ZigBee, and the like.

Figure 4C:
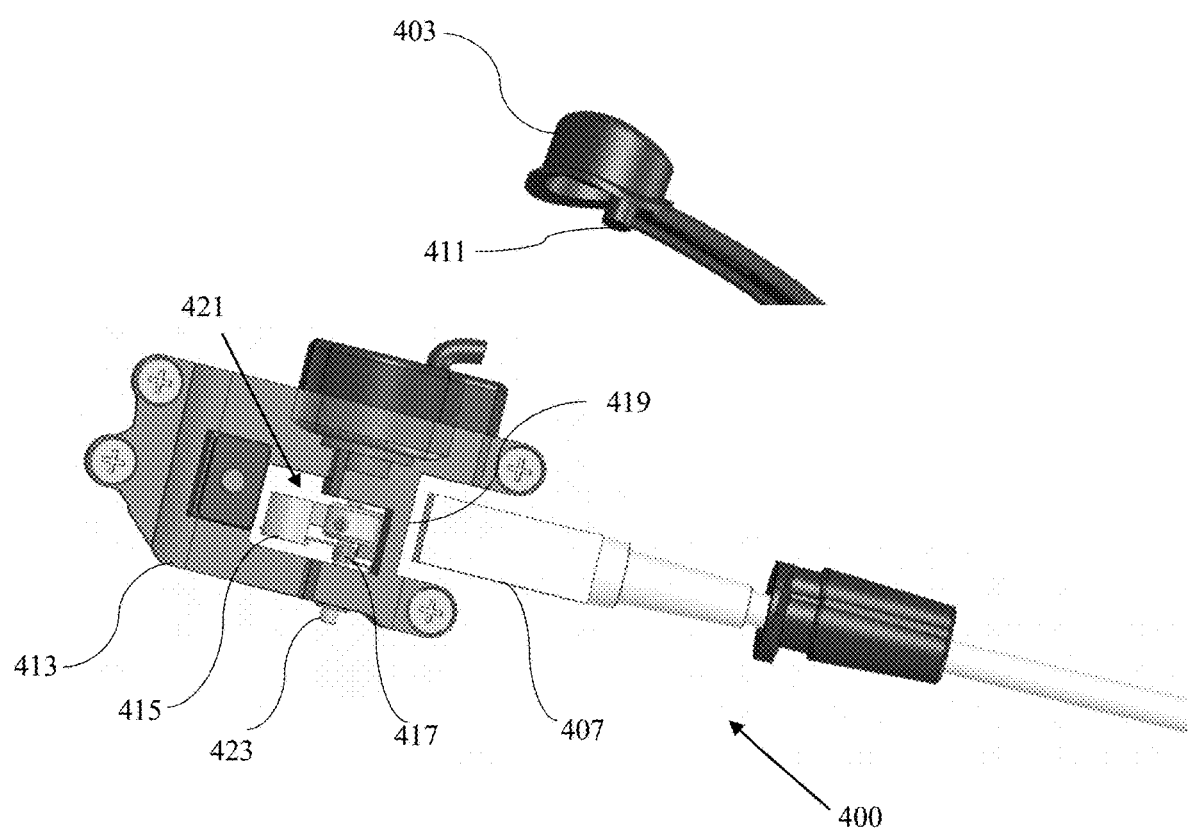
FIG. 4(c) illustrates an exploded view of the surgeon input device in accordance with an embodiment of the disclosure.

FIG. 4(c) illustrates an exploded view of the surgeon input device in accordance with an embodiment of the disclosure. The pinch button (403) as shown in FIG. 4(c) comprises an extruding portion (411) protruding from bottom side of the pinch button (403). The pinch button, as shown in FIG. 4(c), may be flipped around 90 degree so as to show the extruding portion (411). The operating position of the pinch button (403) will be as shown in the FIG. 4(b).

Further, the surgeon input device (400) further comprises of a support structure (413). The support structure (413) may have a portion (419) in which the sensor (407) is disposed. The portion (419) may be a shape similar to the shape of one end of the sensor (407). A lever (415) with a spring (417) is affixed in a hollow recess (421) of the support structure (413) by means of a shaft (423).

In an embodiment, when the surgeon presses the pinch button (403), the extruding portion (411) presses the lever (415) and the at least one sensor (409) may detect the extent to which the lever (415) is pressed and send signal to the control system. Based on the signal received from the at least one sensor (409), the control system regulates the opening and closing of the jaws of the end effector of the surgical instrument. When the surgeon releases the pinch button (403), the extruding portion (411) of the pinch button (403) releases the lever (415) and the spring (417) facilitate the lever to come back to its normal position. Further, the surgeon input device (400) is configured to provide an input to a control system to transform motion of a surgeon's hand into motion of the end-effector of the surgical instrument, instruments actuator, and the robotic arm.

According to an embodiment, a capacitive sensor may be configured with the housing (401) to detect the presence of surgeon's hand. When surgeon holds the surgeon input device (400), the capacitive sensor senses the presence of surgeon's hand and send signal to activate the robotic surgical system (100).

According to another embodiment, the surgeon input device (400) further comprises of a force sensor disposed within the housing (401), where the force sensor configured to detect a pressing and releasing of the at least one button (403).

According to another embodiment, the surgeon input device (400) is configured to provide tactile feedback to the surgeon.

According to another embodiment, the at least one sensor (407) disposed within the housing (401) is an electromagnetic sensor or Inertial Measurement Unit (IMU) sensor.

According to another embodiment, the surgeon input device (400) is in operative communication with the control system via a wired means.

According to another embodiment, the surgeon input device (400) is in operative communication with the control system via a wireless means such as Bluetooth.

According to another embodiment, the surgeon input device (400) may contain a power source, such as a battery pack, contained within the housing (401).

According to another embodiment, the housing (401) is configured to receive control inputs from the surgeon via one or more of translation of the housing (401), rotation of the housing (401), pressing of the outer surface with the surgeon's hand, and changing of the angular orientation of the longitudinal axis of the housing (401).

The surgeon input device (400) may be made of inexpensive materials such as but not limited to soft rubber and plastic. The sensor and the other related electronics may also be inexpensive, thus making the entire surgeon input device (400) inexpensive. Another advantage of using inexpensive materials for the surgeon input device (400) is that the design may be scalable in size. Thus, the surgeon input device (400) of differing sizes may be manufactured to accommodate the various hand sizes of the surgeon. In some embodiments, the surgeon input device (400) may be a disposable component, for e.g., use in a single surgical operation.

The foregoing descriptions of exemplary embodiments of the present disclosure have been presented for purposes of illustration and description. They are not intended to be exhaustive or to limit the disclosure to the precise forms disclosed, and obviously many modifications and variations are possible in light of the above teaching. The exemplary embodiment was chosen and described in order to best explain the principles of the disclosure and its practical application, to thereby enable others skilled in the art to best utilize the disclosure and various embodiments with various modifications as are suited to the particular use contemplated. It is understood that various omissions, substitutions of equivalents are contemplated as circumstance may suggest or render expedient but is intended to cover the application or implementation without departing from the spirit or scope of the claims of the present disclosure.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims. While specific language has been used to describe the disclosure, any limitations arising on account of the same are not intended. As would be apparent to a person in the art, various working modifications may be made to the apparatus in order to implement the inventive concept as taught herein.

While specific language has been used to describe the disclosure, any limitations arising on account of the same are not intended. As would be apparent to a person in the art, various working modifications may be made to the apparatus in order to implement the inventive concept as taught herein.

We claim:

1. A surgeon input device for controlling a robotic surgical system, comprising:
   a housing;
   at least one sensor probe disposed within the housing and the at least one sensor probe, in operative communication with an electromagnetic signal transmitter, configured to detect at least one of a position and orientation of a surgeon's hand within a predefined electromagnetic field generated by the electromagnetic signal transmitter;

a support structure positioned within the housing;

a lever with a spring affixed in a hollow recess of the support structure by means of a shaft;

at least one button protruding out of the housing having an extruding portion and the extruding portion is configured to push the lever; and at least one sensor disposed within the housing, the at least one sensor configured to detect a compression and decompression of the at least one button and send a signal via a sensor wire to a control system to regulate opening and closing of an end effector of a surgical instrument.

2. The surgeon input device of claim 1, wherein the housing comprising a capacitive sensor to detect presence of the surgeon's hand.

3. The surgeon input device of claim 1, wherein the at least one sensor is an electromagnetic sensor or an Inertial Measurement Unit (IMU) sensor.

4. The surgeon input device of claim 1, wherein the surgeon input device in operative communication with the control system via a wireless means such as Bluetooth.

5. The surgeon input device of claim 1, wherein the at least one sensor is an optical sensor.

6. The surgeon input device of claim 1, wherein the at least one sensor is a force sensor.

7. The surgeon input device of claim 1, wherein the surgeon input device configured to provide an input to the control system to transform motion of the surgeon's hand into motion of the end-effector of the surgical instrument.

8. The surgeon input device of claim 1, wherein the surgeon input device is made of polycarbonate plastic.

9. The surgeon input device of claim 1, wherein the housing comprising an outer surface configured to be gripped by the surgeon's hand and to facilitate translation and rotation of the housing by the surgeon's hand.

* * * * *